(12) United States Patent
Evans et al.

(10) Patent No.: US 7,125,863 B2
(45) Date of Patent: *Oct. 24, 2006

(54) INHIBITORS OF DIPEPTIDYL PEPTIDASE IV

(75) Inventors: David Michael Evans, Southampton (GB); Gary Robert William Pitt, Hampshire (GB)

(73) Assignee: Ferring BV, Hoofddorp (NL)

( * ) Notice: Subject to any disclaimer, the term of this patent is extended or adjusted under 35 U.S.C. 154(b) by 388 days.

This patent is subject to a terminal disclaimer.

(21) Appl. No.: 10/258,804

(22) PCT Filed: Apr. 26, 2001

(86) PCT No.: PCT/GB01/01875

§ 371 (c)(1),
(2), (4) Date: Jan. 17, 2003

(87) PCT Pub. No.: WO01/81337

PCT Pub. Date: Nov. 1, 2001

(65) Prior Publication Data

US 2004/0082497 A1 Apr. 29, 2004

(30) Foreign Application Priority Data

Apr. 26, 2000 (GB) ................................ 0010188.1

(51) Int. Cl.
| | | |
|---|---|---|
| A01N 43/00 | (2006.01) | |
| A01N 43/58 | (2006.01) | |
| A01N 43/60 | (2006.01) | |
| A61K 31/5365 | (2006.01) | |
| A61K 31/5385 | (2006.01) | |
| A61K 31/50 | (2006.01) | |
| A61K 31/495 | (2006.01) | |
| C07D 237/28 | (2006.01) | |
| C07D 487/00 | (2006.01) | |
| C07D 455/02 | (2006.01) | |
| C07D 403/02 | (2006.01) | |
| C07D 231/56 | (2006.01) | |
| C07D 231/02 | (2006.01) | |
| C07D 231/04 | (2006.01) | |
| C07D 231/06 | (2006.01) | |

(52) U.S. Cl. ................. 514/210.18; 514/248; 514/249; 514/255.05; 514/259.5; 514/266.2; 514/269; 514/306; 514/307; 514/309; 514/312; 514/314; 514/343; 514/367; 514/368; 514/369; 514/372; 514/373; 514/375; 514/376; 514/379; 514/380; 514/390; 514/394; 514/395; 514/397; 514/405; 514/407; 544/235; 544/237; 544/238; 544/239; 544/282; 544/287; 544/288; 544/316; 544/319; 544/349; 544/354; 544/408; 546/138; 546/141; 546/146; 546/153; 546/279.1; 548/306.1; 548/314.7; 548/361.5; 548/362.5; 548/364.1; 548/154; 548/171; 548/178; 548/187; 548/204; 548/209; 548/213; 548/214; 548/221; 548/228; 548/229; 548/236; 548/241; 548/243; 548/247

(58) Field of Classification Search ................ 544/235, 544/237, 238, 239, 282, 287, 288, 316, 319, 544/349, 354, 408; 546/138, 141, 146, 153, 546/279.1; 548/306.1, 314.7, 361.5, 362.5, 548/364.1, 154, 171, 178, 187, 204, 209, 548/213, 214–221, 228, 229, 236, 241, 243, 548/247; 514/210.18, 248, 249, 255.05, 514/259.5, 266.2, 209, 306, 307, 309, 312, 514/314, 343, 367, 368, 369, 372, 373, 375, 514/376, 379, 380, 390, 394, 395, 397, 405, 514/407

See application file for complete search history.

(56) References Cited

U.S. PATENT DOCUMENTS

| | | |
|---|---|---|
| 5,462,928 A | 10/1995 | Bachovchin et al. |
| 6,011,155 A | 1/2000 | Villhauer |
| 2004/0167341 A1* | 8/2004 | Haffner et al. .............. 548/200 |
| 2004/0171848 A1* | 9/2004 | Haffner et al. .............. 548/517 |

FOREIGN PATENT DOCUMENTS

WO   WO 98/19998 A   5/1998

OTHER PUBLICATIONS

Evans, D. M. "Dipeptidyl Peptidase IV Inhibitors" Investigational Drugs Journal, vol. 5(6), pp. 577-585 (2002).*
Bonnett et al, "Experiments towards the Synthesis of Corrins. Part 1. The Preparation and Reactions of Some delta-1-Pyrrolines. A Novel Proline Synthesis" Journal of the Chemical Society, pp. 2087-2093 (1959).*

(Continued)

*Primary Examiner*—Zachary C Tucker
(74) *Attorney, Agent, or Firm*—Foley & Lardner LLP

(57) ABSTRACT

Compounds according to formula (1), wherein $R^1$ is H or CN, $X^1$ is S, O, $SO_2$ or $CH_2$, $X^2$ is CO, $CH_2$ or a covalent bond, Het is a nitrogen-containing heterocycle and n is 1–5 are new. The compounds of the invention are inhibitors of dipeptidyl peptidase IV. Pharmaceutical compositions of the compounds of the invention, or pharmaceutically acceptable salts thereof, are useful in the treatment of, inter alia, type 2 diabetes

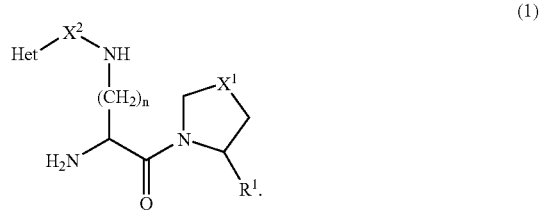

(1)

10 Claims, No Drawings

OTHER PUBLICATIONS

Davey et al, "The Synthesis and Ionisation Constants of Some Fluorenamines" Journal of the Chemical Society [Section C: Organic], pp. 120-123 (1967).*

Sozen and Arici, "Hyperinsulinism and Its Interaction With Hyperandrogenism in Polycystic Ovary Syndrome" Obstetrical and Gynecological Survey, vol. 55(5), pp. 321-328 (2000).*

Goodman & Gilman's The Pharmacological Basis of Therapeutics Tenth Edition, McGraw-Hill Medical Publishing Division © 2001, pp. 1541-1546.*

Bengtsson et al, "Therapeutic Controversy—Treatment of Growth Hormone Deficiency in Adults" Journal of Clinical Endocrinology & Metabolism, vol. 85(3), pp 933-942 (2000).*

* cited by examiner

INHIBITORS OF DIPEPTIDYL PEPTIDASE IV

The present invention relates to a series of novel compounds that are inhibitors of the enzyme dipeptidyl peptidase IV, to pharmaceutical compositions comprising these inhibitors, and the use of such compositions in the treatment of human diseases.

BACKGROUND

The enzyme dipeptidyl peptidase IV, herein abbreviated DP-IV (and elsewhere as DAP-IV or DPP-IV) and also known by the classification EC.3.4.14.5, is a serine protease that cleaves the N-terminal dipeptide from peptides that begin with the sequence H-Xaa-Pro (where Xaa is any amino acid, although preferably a lipophilic one, and Pro is proline). It will also accept as substrates peptides that begin with the sequence H-Xaa-Ala (where Ala is alanine). DP-IV was first identified as a membrane-bound protein. More recently a soluble form has been identified.

Initial interest in DP-IV focussed on its role in the activation of T lymphocytes. DP-IV is identical to the T cell protein CD26. It was proposed that inhibitors of DP-IV would be capable of modulating T cell responsiveness, and so could be developed as novel immunomodulators. It was further suggested that CD26 was a necessary co-receptor for HIV, and thus that DP-IV inhibitors could be useful in the treatment of AIDS.

Attention was given to the role of DP-IV outside the immune system. It was recognised that DP-IV has a key role in the degradation of several peptide hormones, including growth hormone releasing hormone (GHRH) and glucagon-like peptide-1 and -2 (GLP-1 and GLP-2). Since GLP-1 is known to have a potentiating effect on the action of insulin in the control of post-prandial blood glucose levels it is clear that DP-IV inhibitors might also be usefully employed in the treatment of type II diabetes and impaired glucose tolerance. At least two DP-IV inhibitors are currently undergoing clinical trials to explore this possibility.

Several groups have disclosed inhibitors of DP-IV. While some leads have been found from random screening programs, the majority of the work in this field has been directed towards the investigation of substrate analogs. Inhibitors of DP-IV that are substrate analogs are disclosed in, for example, U.S. Pat. No. 5,462,928, U.S. Pat. No. 5,543,396, WO95/15309 (equivalent to U.S. Pat. No. 5,939,560 and EP 0731789), WO98/19998 (equivalent to U.S. Pat. No. 6,011,155), WO99/46272 and WO99/61431. The most potent inhibitors are aminoacyl pyrrolidine boronic acids, but these are unstable and tend to cyclise, while the more stable pyrrolidine and thiazolidine derivatives have a lower affinity for the enzyme and so would require large doses in a clinical situation. Pyrrolidine nitriles appear to offer a good compromise since they have both a high affinity for the enzyme and a reasonably long half-life in solution as the free base. There remains, however, a need for inhibitors of DP-IV with improved properties.

BRIEF DESCRIPTION OF THE INVENTION

The present invention relates to a series of inhibitors of DP-IV with improved affinity for the enzyme. The compounds can be used for the treatment of a number of human diseases, including impaired glucose tolerance and type II diabetes. Accordingly, the invention further relates to the use of the compounds in the preparation of pharmaceutical compositions, to such compositions per se, and to the use of such compositions in human therapy. The compounds of the invention are described by general formula 1.

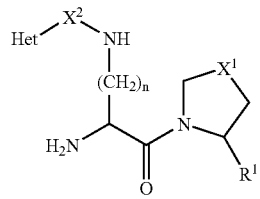

In general formula 1, $R^1$ is either H or CN, $X^1$ is S, O, $SO_2$ or $CH_2$, $X^2$ is a carbonyl group, $CH_2$ or is absent, n is 1–5, and Het is an optionally substituted aromatic nitrogen-containing heterocycle.

DETAILED DESCRIPTION OF THE INVENTION

In a first aspect, the present invention comprises a series of novel compounds that are inhibitors of the enzyme DP-IV and are useful for the treatment of certain human diseases. The compounds are described by general formula 1.

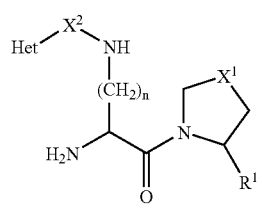

In this general formula, $R^1$ represents either a hydrogen atom or a nitrile group (—C≡N). $X^1$ represents a sulphur atom, an oxygen atom, a sulphonyl group (—$SO_2$—) or a methylene group (—$CH_2$—). $X^2$ represents either a carbonyl group (>C=O), a methylene group (—$CH_2$—) or a covalent bond. The variable n can have any integral value between 1 and 5. Het represents an aromatic nitrogen-containing heterocycle selected from pyridyl, pyridazinyl, pyrimidinyl, pyrazinyl, imidazolyl, pyrazolyl, thiazolyl, isothiazolyl, oxazolyl, isoxazolyl and benz-fused analogues thereof, such as quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl and benzisoxazolyl. This heterocycle may optionally be substituted on one or more carbon atoms. Suitable substituents are lower alkyl, hydroxy, lower alkyloxy, amino, lower alkylamino, di(lower alkyl)amino, fluoro, chloro, bromo, nitro, trifluoromethyl, cyano, carboxy and lower alkyloxycarbonyl groups.

In the context of the present disclosure, the term lower alkyl, either by itself or in such combinations as lower alkyloxy, is intended to comprise linear, branched and cyclic saturated hydrocarbon groups of between one and six carbon atoms. Examples of lower alkyl groups include, but are not limited to, methyl, ethyl, isopropyl, tert-butyl, neopentyl, cyclohexyl, cyclopentylmethyl, 2-(cyclopropyl)ethyl, 3,3-dimethylcyclobutyl and bicyclo[3.1.0]hexyl.

The compounds of general formula 1 have at least one stereogenic centre and so can exhibit optical isomerism. All such isomers, including enantiomers, diastereomers and epimers are included within the scope of the invention. Furthermore, the invention includes such compounds as single isomers and as mixtures, including racemates. Certain compounds according to general formula 1, including those in which the Het group carries a hydroxy or amino substituent, can exist as tautomers. These tautomers, either separately or as mixtures, are also considered to be within the scope of the invention.

The compounds according to general formula 1 have at least one basic functional group. They can therefore form addition salts with acids. Those addition salts that are formed with pharmaceutically acceptable acids are included within the scope of the invention. Examples of suitable acids include acetic acid, trifluoroacetic acid, citric acid, fumaric acid, benzoic acid, pamoic acid, methanesulphonic acid, hydrochloric acid, nitric acid, sulphuric acid, phosphoric acid and the like.

Certain compounds according to general formula 1 have an acidic group and so are able to form salts with bases. Examples of such salts include the sodium, potassium and calcium salts, which are formed by the reaction of the acid with the corresponding metal hydroxide, oxide, carbonate or bicarbonate. Similarly, tetra-alkyl ammonium salts may be formed by the reaction of the acid with a tetra-alkyl ammonium hydroxide. Primary, secondary and tertiary amines, such as triethylamine, can form addition salts with the acid. A particular case of this would be an internal addition salt formed between an acidic group and the primary amine group of the same molecule, which is also called a zwitterion. Insofar as they are pharmaceutically acceptable, all these salts are included within the scope of the invention.

In a preferred embodiment of the invention $R^1$ is a nitrile group. Within this embodiment, it is preferred that the stereochemistry of the nitrile group is as shown in general formula 2.

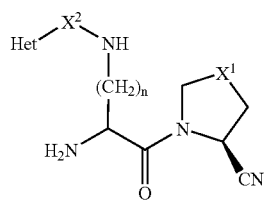

2

According to the standard terminology, this is the S configuration when $X^1$ is methylene but the R configuration when $X^1$ is sulphur, oxygen or sulphonyl.

In another preferred embodiment, the stereochemistry at the centre adjacent to the primary amine is the S configuration as shown in general formula 3.

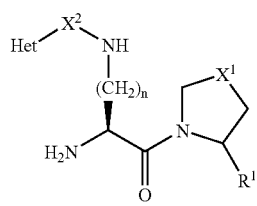

3

Within this embodiment, it is more preferred that $R^1$ should be a nitrile group, and more preferred still that it should have the absolute configuration depicted in general formula 4.

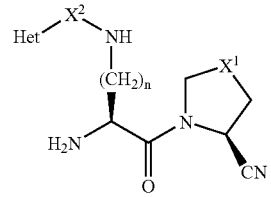

4

In another preferred embodiment of the invention, $X^1$ is a sulphur atom or a methylene group.

In another preferred embodiment of the invention, n is 3 or 4.

Particularly preferred compounds within the invention include:
(2S)-1-[N$^\omega$-(Pyrazinyl-2-carbonyl)-L-ornithinyl]pyrrolidine-2-carbonitrile,
(2S)-1-[N$^\omega$-(Pyrazinyl-2-carbonyl)-L-lysinyl]pyrrolidine-2-carbonitrile,
(2S)-1-[(2'S)-2'-Amino-4'-(pyrazinyl-2"-carbonylamino)butanoyl]pyrrolidine-2-carbonitrile,
(4R)-3-[N$^\omega$-(Pyrazinyl-2-carbonyl)-L-lysinyl]thiazolidine-4-carbonitrile,
1-[N$^\omega$-(Pyrazinyl-2-carbonyl)-L-ornithinyl]pyrrolidine,
3[N$^\omega$-(2-Chloropyridyl-3-carbonyl)-L-ornithinyl]thiazolidine,
1-[N$^\omega$-(2-Chloropyridyl-3-carbonyl)-L-ornithinyl]pyrrolidine,
(2S)-1-[N$^\omega$-(2-Chloropyridyl-3-carbonyl)-L-ornithinyl]pyrrolidine-2-carbonitrile,
3-[N$^\omega$-(Pyrazinyl-2-carbonyl)-L-ornithinyl]thiazolidine,
3-[N$^\omega$-(5-Cyano-2-pyridyl)-L-lysinyl]thiazolidine,
(2S)-1-[N$^\omega$-(5-Cyano-2-pyridyl)-L-lysinyl]pyrrolidine-2-carbonitrile,
(2S)-1-[N$^\omega$-(5-Trifluoromethyl-2-pyridyl)-L-ornithinyl]pyrrolidine-2-carbonitrile,
3-[N$^\omega$-(2-Quinolinylmethyl)-L-lysinyl]thiazolidine,
3-[N$^\omega$-(2-Quinolinylmethyl)-L-ornithinyl]thiazolidine,
3-[N$^\omega$-(2-Quinoxaloyl)-L-lysinyl]thiazolidine,
3-[N$^\omega$-(2-Quinoxaloyl)-L-ornithinyl]thiazolidine,
(2S)-1-[N$^\omega$-(2-Quinoxaloyl)-L-ornithinyl]pyrrolidine-2-carbonitrile,
3-[N$^\omega$-(6-Methylpyrazinyl-2-carbonyl)-L-ornithinyl]thiazolidine,
3-[N$^\omega$-(Isoquinoline-3-carbonyl)-L-ornithinyl]thiazolidine, and
3-[N$^\omega$-(6-Trifluoromethylnicotinoyl)-L-ornithinyl]thiazolidine.

In a second aspect, the present invention comprises a pharmaceutical composition for human therapeutic use. The composition is characterised in that it has, as an active agent, at least one of the compounds described above. Such a composition is useful in the treatment of human diseases. The composition will generally include one or more additional components selected from pharmaceutically acceptable excipients and pharmaceutically active agents other than those of the present invention.

The composition may be presented as a solid or liquid formulation, depending on the intended route of administration. Examples of solid formulations include pills, tablets, capsules and powders for oral administration, suppositories for rectal or vaginal administration, powders for nasal or pulmonary administration, and patches for transdermal or transmucosal (such as buccal) administration. Examples of liquid formulations include solutions and suspensions for intravenous, subcutaneous or intramuscular injection and oral, nasal or pulmonary administration. A particularly preferred presentation is a tablet for oral administration. Another preferred presentation, particularly for emergency and critical care, is a sterile solution for intravenous injection.

The composition comprises at least one compound according to the preceding description. The composition may contain more than one such compound, but in general it is preferred that it should comprise only one. The amount of the compound used in the composition will be such that the total daily dose of the active agent can, be administered in one to four convenient dose units. For example, the composition can be a tablet containing an amount of compound equal to the total daily dose necessary, said tablet to be taken once per day. Alternatively, the tablet can contain half (or one third, or one quarter) of the daily dose, to be taken twice (or three or four times) per day. Such a tablet can also be scored to facilitate divided dosing, so that, for example, a tablet comprising a full daily dose can be broken into half and administered in two portions. Preferably, a tablet or other unit dosage form will contain between 0.1 mg and 1 g of active compound. More preferably, it will, contain between 1 mg and 250 mg.

The composition will generally include one or more excipients selected from those that are recognised as being pharmaceutically acceptable. Suitable excipients include, but are not limited to, bulking agents, binding agents, diluents, solvents, preservatives and flavouring agents. Agents that modify the release characteristics of the composition, such as polymers that selectively dissolve in the intestine ("enteric coatings") are also considered in the context of the present invention, to be suitable excipients.

The composition may comprise, in addition to the compound of the invention, a second pharmaceutically active agent. For example, the composition may include an anti-diabetic agent, a growth-promoting agent, an anti-inflammatory agent or an antiviral agent. However, it is generally preferred that the composition comprise only one active agent.

In a third aspect, the invention comprises a use for the compounds and compositions described above for the treatment of human diseases. This aspect can equally be considered to comprise a method of treatment for such diseases. The diseases susceptible to treatment are those wherein an inhibition of DP-IV or CD26 results in a clinical benefit either directly or indirectly. Direct effects include the blockade of T lymphocyte activation. Indirect effects include the potentiation of peptide hormone activity by preventing the degradation of these hormones. Examples of diseases include, but are not limited to, auto-immune and inflammatory diseases such as inflammatory bowel disease and rheumatoid arthritis, growth hormone deficiency leading to short stature, polycystic ovary syndrome, impaired glucose tolerance and type 2 diabetes. Particularly preferred is the use of the compounds and compositions for the treatment of impaired glucose tolerance and type 2 diabetes, and equally a method of treatment of these diseases by the administration of an effective amount of a compound or composition as previously described.

The precise details of the treatment, including the dosing regimen, will be established by the attending physician taking into account the general profile of the patient and the severity of the disease. For diseases such as inflammatory bowel disease that have acute phases of active disease separated by quiescent periods, the physician may select a relatively high dose during the acute phase and a lower maintenance dose for the quiescent period. For chronic diseases such as type 2 diabetes and impaired glucose tolerance, the dosing may need to be maintained at the same level for an extended period. A dosing schedule of one to four tablets per day, each comprising between 0.1 mg and 1 g (and preferably between 1 mg and 250 mg) of active compound might be typical in such a case.

The compounds according to the invention can be prepared by methods known in the art. The route chosen will depend on the particular nature of the substituents present in the target molecule. The starting material will usually be an α,ω-diamino acid derivative 5.

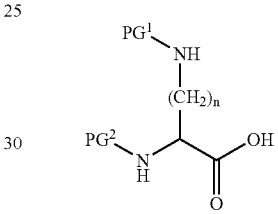

5

$PG^1$ and $PG^2$ are "orthogonal" protecting groups—groups that mask the reactivity of the amine groups and that can each be selectively removed in the presence of the other. Suitable groups are well known in the literature. Derivatives of diamino acids according to general formula 5 are either items of commerce, or are described in the literature, for all values of n in the range 1 to 5 and for both the R and the S stereoisomer.

For some synthetic strategies, it is preferable to start with an ester of the above diamino acid, such as the benzyl, methyl or tert-butyl ester. The ester will be chosen such that it is not hydrolysed by reagents that can cleave $PG^1$ or $PG^2$.

Starting from 5, it is necessary to elaborate the acid function into the pyrrolidine amide derivative of the target molecule, and to elaborate the ω-amine function into the desired heteroaryl derivative. The order in which these two steps are performed is not necessarily important.

Scheme A

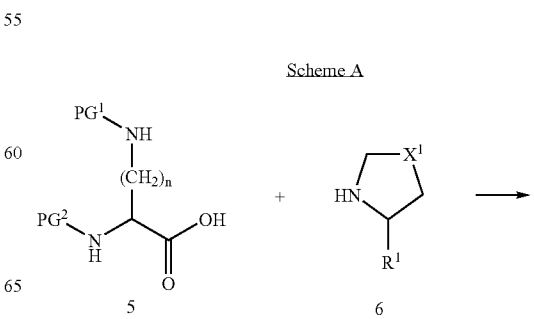

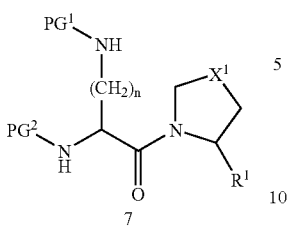

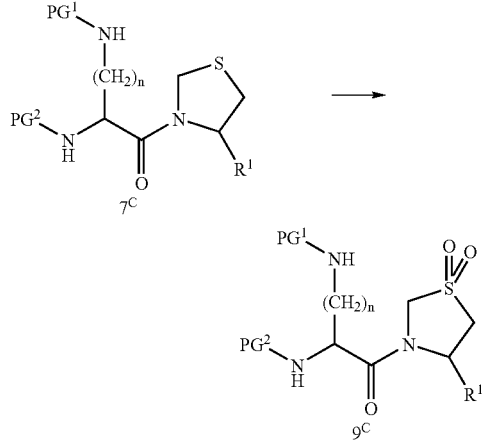

The diamino acid derivative 5 can be reacted with a pyrrolidine derivative 6 to give the amide 7. Reaction conditions for achieving this transformation are well known in the literature. Suitable reagents include carbodiimides, phosphorus reagents and alkyl chloroformates, and the reaction is usually catalysed by a tertiary amine such as triethylamine or dimethylaminopyridine.

The reaction depicted in Scheme A is available for all combinations of $R^1$ and $X^1$. However, for the case where $R^1$ is a nitrile group, or where $X^1$ is a sulphonyl group, it may be advantageous to modify the strategy as depicted in Schemes B and C.

In Scheme B, the $R^1$ group is introduced as a primary amide and subsequently transformed into a nitrile by the action of a dehydrating agent such as trifluoroacetic anhydride. In Scheme C, the $X^1$ group is introduced as a thioether and subsequently transformed into a sulphone by the action of an oxidant such as sodium periodate.

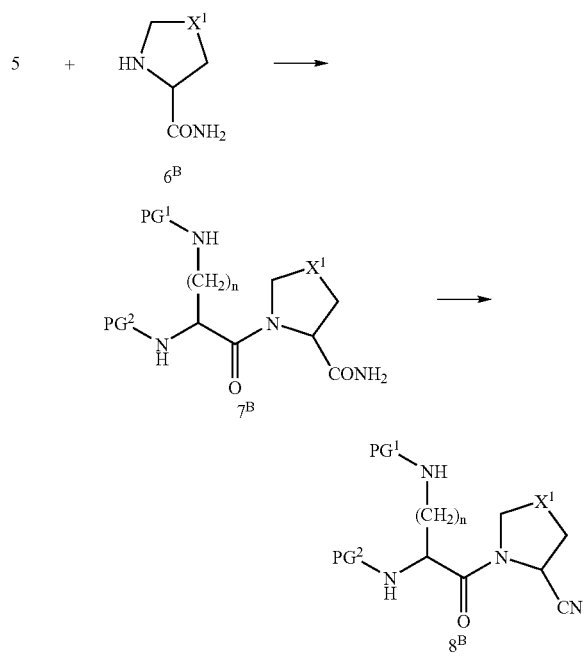

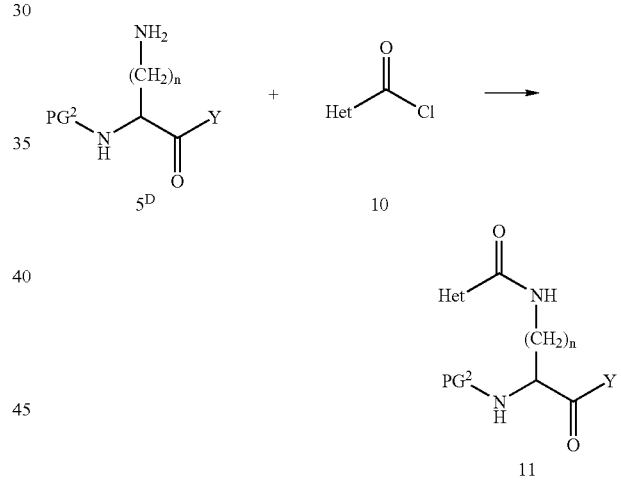

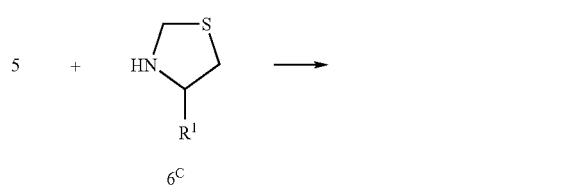

In Scheme D, compound $5^D$ is the diamino acid derivative 5 after removal of the ω-protecting group. Y may represent OH, but more usually will represent the pyrrolidine ring or the O-alkyl group of an ester. The free amine group is reacted with a heteroaryl carbonyl chloride to produce an amide 11, which incorporates the functionality of the compounds of the invention wherein $X^2$ is a carbonyl group. Heteroaryl carbonyl chlorides are easily prepared from the corresponding carboxylic acids, which are well known compounds. The reaction of scheme D is generally applicable to all the variations of the group Het, with the proviso that certain substituents on Het may require protection. Such groups and the appropriate protection will generally be obvious to those familiar with the art.

When $X^2$ is a covalent bond, it may still be possible to obtain the target functionality from the amine $5^D$ by direct reaction with a heteroaryl chloride or fluoride. In some cases, the heteroaryl chloride or fluoride may not be easily accessible, or may not be sufficiently reactive, and it will then be necessary to use an alternative route, such as a reductive amination. This is illustrated in Scheme E.

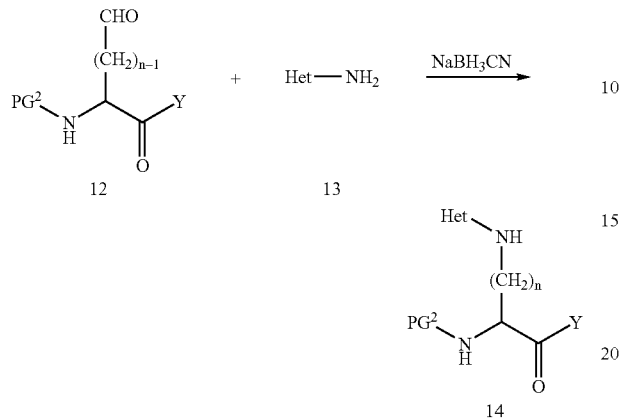

Reductive amination is also the method of choice when $X^2$ is a methylene group. In this case, there are two options, as illustrated in Scheme F.

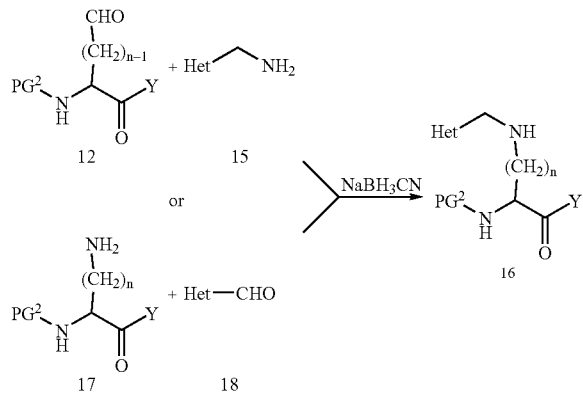

When all the groups have been elaborated the final protecting group is removed and the product is isolated and purified using standard techniques.

These general methods are further illustrated in the following, non-limiting examples.

EXAMPLES

Abbreviations

The following abbreviations have been used.

| | |
|---|---|
| DMF | N,N-Dimethyformamide |
| h | Hour(s) |
| hplc | High pressure liquid chromatography |
| min | Minute(s) |
| pet. ether | Petroleum ether fraction boiling at 60–80° C. |
| PyBOP ® | (Benzotriazol-1-yloxy)tripyrrolidinophosphonium hexafluorophosphate |
| PyBroP ® | Bromotripyrrolidinophosphonium hexafluorophosphate |
| TFA | Trifluoroacetic acid |

Example 1

(2S)-1-[N$^\omega$-(Pyrazinyl-2-carbonyl)-L-ornithinyl] pyrrolidine-2-carbonitrile trifluoroacetate

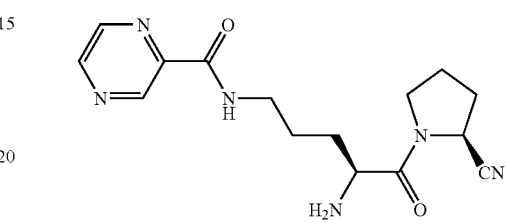

A. N-(2-Nitrobenzenesulphenyl)-L-proline

L-Proline (25 g, 217 mmol) was dissolved in 2M NaOH (110 mL, 220 mmol) and dioxan (120 mL). A solution of 2-nitrobenzenesulphenyl chloride (42 g, 222 mmol) in dioxan (60 mL) was slowly added at the same time as 2M NaOH (110 mL, 220 mmol). After 2 h at room temperature the reaction mixture was poured into water (500 mL) and the solid filtered off. The pH of the filtrate was adjusted to pH3 with 2M HCl and the solution was extracted with ethyl acetate (3×500 mL). The combined organic extracts were washed with water (4×200 mL) and brine (1×200 mL), dried (Na$_2$SO$_4$) and evaporated in vacuo to give an orange solid identified as N-(2-nitrobenzenesulphenyl)-L-proline (58.1 g, 217 mmol, 100%).

B. N-(2-Nitrobenzenesulphenyl)-L-proline succinimidyl ester

N-(2-Nitrobenzenesulphenyl)-L-proline (57.9 g, 216 mmol) was dissolved in CH$_2$Cl$_2$/DMF (9:1, 500 mL). N-Hydroxysuccinimide (37.3 g, 324 mmol) and water-soluble carbodiimide (51.8 g, 260 mmol) were added. After 18 h at room temperature the solvent was removed in vacuo and the residue was taken up in ethyl acetate (1000 mL). The solution was washed with water (4×200 mL) and brine (1×200 mL), dried (Na$_2$SO$_4$) and evaporated in vacuo to give a yellow solid identified as N-(2-nitrobenzenesulphenyl)-L-proline succinimidyl ester (78.9 g, 216 mmol, 100%).

C. N-(2-Nitrobenzenesulphenyl)-L-prolinamide

N-(2-Nitrobenzenesulphenyl)-L-proline succinimidyl ester (78.5 g, 215 mmol) was dissolved in dioxan (500 mL). Ammonia (35%, 100 mL) was added. After stirring at room temperature for 2 h the reaction mixture was poured into water (700 mL). The precipitate was filtered off, washed with water (200 mL), dried over P$_2$O$_5$ and recrystallised from ethyl acetate/pet ether to give a yellow solid identified as N-(2-nitrobenzenesulphenyl)-L-prolinamide (49.6 g, 185 mmol, 86%).

D. (2S)-N-(2-Nitrobenzenesulphenyl)pyrrolidine-2-carbonitrile

N-(2-Nitrobenzenesulphenyl)-L-prolinamide (49 g, 183 mmol) was dissolved in dry THF(300 mL). The solution was cooled to 0° C., triethylamine (36.7 g, 367 mmol) was added followed by the slow addition of trifluoroacetic anhydride (77 g, 367 mmol). The pH was adjusted to pH9 with triethylamine. After 30 min the reaction mixture was diluted with ethyl acetate (500 mL), washed with water (1×200 mL) and brine (1×200 mL), dried ($Na_2SO_4$) and evaporated in vacuo to give an orange oil which was purified by flash chromatography (eluant: 80% pet ether, 20% ethyl acetate) to give a yellow solid identified as (2S)-N-(2-nitrobenzenesulphenyl)pyrrolidine-2-carbonitrile (38.9 g, 150 mmol, 82%).

E. (2S)-Pyrrolidine-2-carbonitrile hydrochloride (2S)-N-(2-Nitrobenzenesulphenyl)pyrrolidine-2-carbonitrile (38.5 g, 149 mmol) was dissolved in diethyl ether (200 mL). 4M HCl/Dioxan (150 mL, 600 mmol) was slowly added. After 2 h at room temperature the reaction mixture was poured into diethyl ether (1000 mL). The solid was filtered off, washed with diethyl ether (500 mL) and recrystallised from methanol/diethyl ether to give a white solid identified as (2S)-pyrrolidine-2-carbonitrile hydrochloride (18.9 g, 142.5 mmol, 96%).

F. (2S)-1-[$N^\alpha$-(tert-Butyloxycarbonyl)-$N^\omega$-(pyrazinyl-2-carbonyl)-L-ornithinyl]-pyrrolidine-2-carbonitrile.

$N^\alpha$-(tert-Butyloxycarbonyl)-$N^\omega$-(pyrazinyl-2-carbonyl)-L-ornithine (2.5 g, 7.4 mmol) was dissolved in $CH_2Cl_2$ (50 mL). This solution was cooled to 0° C., (2S)-pyrrolidine-2-carbonitrile hydrochloride (1.2 g, 9.1 mmol) and PyBOP® (4.3 g, 8.23 mmol) were added, and the pH adjusted to pH9 with triethylamine. After 18 h at 0° C. to room temperature the solvent was removed in vacuo and the residue was taken up in ethyl acetate (200 mL). This solution was washed with 0.3M $KHSO_4$ (2×50 mL), sat. $NaHCO_3$ (2×50 mL), water (2×50 mL) and brine (1×50 mL), dried ($Na_2SO_4$) and evaporated in vacuo to give a yellow oil. This was purified by flash chromatography (eluant: 80% ethyl acetate, 20% pet. ether) to give a colourless oil identified as (2S)-1-[$N^\alpha$-(tert-butyloxycarbonyl)-$N^\omega$-(pyrazinyl-2-carbonyl)-L-ornithinyl]pyrrolidine-2-carbonitrile (2.98 g, 7.16 mmol, 97%).

G. (2S)-1-[$N^\omega$-(pyrazinyl-2-carbonyl)-L-ornithinyl]pyrrolidine-2-carbonitrile trifluoroacetate (2S)-1-[$N^\alpha$-tert-Butyloxycarbonyl-$N^\omega$-(pyrazinyl-2-carbonyl)-L-ornithinyl]pyrrolidine-2-carbonitrile (2.8 g, 6.7 mmol) was dissolved in trifluoroacetic acid (5 mL). After 1 h at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as (2S)-1-[$N^\omega$-(pyrazinyl-2-carbonyl)-L-ornithinyl]pyrrolidine-2-carbonitrile trifluoroacetate (1.5 g, 3.48 mmol, 52%).

$[M+H]^+=317.3$

Example 2

(2S)-1-[$N^\omega$-(Pyrazinyl-2-carbonyl)-L-lysinyl]pyrrolidine-2-carbonitrile trifluoroacetate

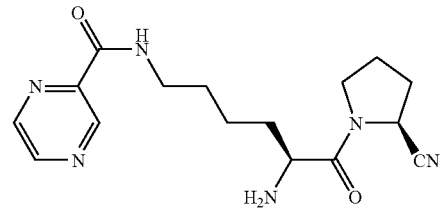

A. ($N^\alpha$-(tert-Butyloxycarbonyl)-$N^\omega$-(9-fluorenylmethyloxycarbonyl)-L-lysinyl)-L-prolinamide $N^\alpha$-(tert-Butyloxycarbonyl)-$N^\omega$-(9-fluorenylmethyloxycarbonyl)-L-lysine (5 g, 10.7 mmol) was dissolved in $CH_2Cl_2$ (100 mL). The solution was cooled to 0° C., L-prolinamide (1.78 g, 11.7 mmol) and PyBOP® (6.7 g, 12.8 mmol) were added, and the pH adjusted to pH9 with triethylamine. After 18 h at 0° C. to room temperature the solvent was removed in vacuo and the residue was taken up in ethyl acetate (200 mL). The solution was washed with 0.3M $KHSO_4$ (2×50 mL), sat. $NaHCO_3$ (2×50 mL), water (2×50 mL) and brine (1×50 mL), dried ($Na_2SO_4$) and evaporated in vacuo. The residue was purified by flash chromatography (eluant: 2% methanol, 98% chloroform) to give a colourless oil identified as ($N^\alpha$-(tert-butyloxycarbonyl)-$N^\omega$-(9-fluorenylmethyloxycarbonyl)-L-lysinyl)-L-prolinamide (4.05 g, 7.2 mmol, 67%).

B. (2S)-1-($N^\alpha$-(tert-Butyloxycarbonyl)-$N^\omega$-(9-fluorenylmethyloxycarbonyl)-L-lysinyl)-pyrrolidine-2-carbonitrile ($N^\alpha$-(tert-Butyloxycarbonyl)-$N^\omega$-(9-fluorenylmethyloxycarbonyl)-L-lysinyl)-L-prolinamide (3.95 g, 7.02 mmol) was dissolved in dry THF (100 mL). The solution was cooled to 0° C., triethylamine (1.4 g, 14 mmol) was added followed by the slow addition of trifluoroacetic anhydride. (2.97 g, 14.1 mmol). The pH was adjusted to pH9 with triethylamine. After 30 min the reaction mixture was diluted with ethyl acetate (100 mL), washed with water (1×50 mL) and brine (1×50 mL), dried ($Na_2SO_4$) and evaporated in vacuo to give an orange oil. The residue was purified by flash chromatography (eluant: 60% pet ether, 40% ethyl acetate) to give a colourless oil identified as (2S)-1-($N^\alpha$-(tert-butyloxycarbonyl)-$N^\omega$-(9-fluorenylmethyloxycarbonyl)-L-lysinyl)pyrrolidine-2-carbonitrile (3.3 g, 6.11 mmol, 87%).

C. (2S)-1-($N^\alpha$-(tert-Butyloxycarbonyl)-L-lysinyl)pyrrolidine-2-carbonitrile (2S)-1-($N^\alpha$-(tert-Butyloxycarbonyl)-$N^\omega$-(9-fluorenylmethyloxycarbonyl)-L-lysinyl)pyrrolidine-2-carbonitrile (3.1 g, 5.7 mmol) was dissolved in THF (80 mL). Diethylamine (20 mL) was added. After 2 h at room temperature the solvent was removed in vacuo. The residue was purified by flash chromatography (eluant: 90% chloroform, 7% methanol, 3% triethylamine) to give a colourless oil identified as (2S)-1-(N$^\alpha$-(tert-butyloxycarbonyl)-L-lysinyl)pyrrolidine-2-carbonitrile (1.63 g, 5.03 mmol, 89%).

D. (2S)-1-(N$^\alpha$-(tert-Butyloxycarbonyl)-N$^\omega$-(pyrazinyl-2-carbonyl)-L-lysinyl)pyrrolidine-2-carbonitrile (2S)-1-(N$^\alpha$-(tert-Butyloxycarbonyl)-L-lysinyl)pyrrolidine-2-carbonitrile (100 mg, 0.31 mmol) was dissolved in CH$_2$Cl$_2$/DMF (9:1, 20 mL). To this solution at 0° C. was added. 1-hydroxybenzotriazole hydrate (84 mg, 0.62 mmol), water-soluble carbodiimide (76 mg, 0.38 mmol), 2-pyrazinecarboxylic acid (43 mg, 0.35 mmol) and triethylamine (65 mg, 0.65 mmol). After 18 h at 0° C. to room temperature the solvent was removed in vacuo and the residue was taken up in ethyl acetate (70 mL). This solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo to give a yellow oil. The residue was purified by flash chromatography (eluant: 2% methanol, 98% chloroform) to give a colourless oil identified as (2S)-1-(N$^\alpha$-(tert-butyloxycarbonyl)-N$^\omega$-(pyraziny-2-carbonyl)-L-lysinyl)pyrrolidine-2-carbonitrile (124 mg, 0.29 mmol, 93%).

E. (2S)-1-[N$^\omega$-(Pyrazinyl-2-carbonyl)-L-lysinyl]pyrrolidine-2-carbonitrile trifluoroacetate (2S)-1-(N$^\alpha$-(tert-Butyloxycarbonyl)-N$^\omega$-(pyrazinyl-2-carbonyl)-L-lysinyl)pyrrolidine-2-carbonitrile (110 mg, 0.26 mmol) was dissolved in trifluoroacetic acid (5 mL). After 1 h at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as (2S)-1-[N$^\omega$-(pyrazinyl-2-carbonyl)-L-lysinyl]pyrrolidine-2-carbonitrile trifluoroacetate (66 mg).

[M+H]$^+$=331.1

Example 3

(4R)-3-[N$^\omega$-(Pyrazinyl-2-carbonyl)-L-lysinyl]thiazolidine-4-carbonitrile trifluoroacetate

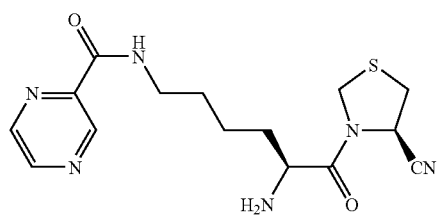

A. (4R)-3-(tert-Butyloxycarbonyl)thiazolidine-4-carboxamide (4R)-3-(tert-Butyloxycarbonyl)thiazolidine-4-carboxylic acid (12.5 g, 54.1 mmol) was dissolved in CH$_2$Cl$_2$/DMF (9:1, 150 mL). To this solution at 0° C. was added 1-hydroxybenzotriazole hydrate (14.6 g, 108 mmol) and water-soluble carbodiimide (13.0 g, 65 mmol). After 1 h at 0° C. ammonia (35%, 50 mL) was added. After 18 h at 0° C. to room temperature the solvent was removed in vacuo and the residue was taken up in ethyl acetate (500 mL). The solution was washed with 0.3M KHSO$_4$ (2×100 mL), sat. NaHCO$_3$ (2×100 mL), water (2×100 mL) and brine (1×100 mL), dried (Na$_2$SO$_4$) and evaporated in vacuo to give a yellow oil. The residue was purified by flash chromatography (eluant: 2% methanol, 98% chloroform) to give a colourless oil identified as (4R)-3-(tert-butyloxycarbonyl)thiazolidine-4-carboxamide (8.9 g, 38.4 mmol, 71%).

B. (4R)-Thiazolidine-4-carboxamide hydrochloride (4S)-3-(tert-Butyloxycarbonyl)thiazolidine-4-carboxamide (8.6 g, 37.1 mmol) was dissolved in 4M HCl/dioxan (50 mL). After 1 h at room temperature the solvent was evaporated in vacuo to give a white solid identified as (4R)-thiazolidine-4-carboxamide hydrochloride (6.2 g, 36.8 mmol, 99%).

C. (4R)-3-[N$^\alpha$-(tert-Butyloxycarbonyl)-N$^\omega$-(9-fluorenylmethyloxycarbonyl)-L-lysinyl]-thiazolidine-4-carboxamide N$^\alpha$-(tert-Butyloxycarbonyl)-N$^\omega$-(9-fluorenylmethyloxycarbonyl)-L-lysine (5 g, 10.7 mmol) was dissolved in CH$_2$Cl$_2$ (100 mL). This solution was cooled to 0° C., (4R)-thiazolidine-4-carboxamide hydrochloride (1.78 g, 11.7 mmol) and PyBOP® (6.7 g, 12.8 mmol) were added, and the pH was adjusted to pH9 with triethylamine. After 18 h at 0° C. to room temperature the solvent was removed in vacuo and the residue was taken up in ethyl acetate (200 mL). The solution was washed with 0.3M KHSO$_4$ (2×50 mL), sat. NaHCO$_3$ (2×50 mL), water (2×50 mL) and brine (1×50 mL), dried (Na$_2$SO$_4$) and evaporated in vacuo to give a yellow oil. The residue was purified by flash chromatography (eluant: 2% methanol, 98% chloroform) to give a colourless oil identified as (4R)-3-[N$^\alpha$-(tert-butyloxycarbonyl)-N$^\omega$-(9-fluorenylmethyloxycarbonyl)-L-lysinyl]thiazolidine-4-carboxamide (2.81 g, 4.8 mmol, 44%).

D. (4R)-3-[N$^\alpha$-(tert-Butyloxycarbonyl)-N$^\omega$-(9-fluorenylmethyloxycarbonyl)-L-lysinyl]-thiazolidine-4-carbonitrile (4R)-3-[N$^\alpha$-(tert-Butyloxycarbonyl)-N$^\omega$-(9-fluorenylmethyloxycarbonyl)-L-lysinyl]thiazolidine-4-carboxamide (2.7 g, 4.7 mmol) was dissolved in dry THF (100 mL). The solution was cooled to 0° C., triethylamine (1.0 g, 10 mmol) was added followed by the slow addition of trifluoroacetic anhydride (2.0 g, 9.5 mmol). The pH was adjusted to pH9 with triethylamine. After 30 min the reaction mixture was diluted with ethyl acetate (100 mL), washed with water (1×50 mL) and brine (1×50 mL), dried (Na$_2$SO$_4$) and evaporated in vacuo. The residue was purified by flash chromatography (eluant: 60% pet ether, 40% ethyl acetate) to give a colourless oil identified as (4R)-3-[N$^\alpha$-(tert-butyloxycarbonyl)-N$^\omega$-(9-fluorenylmethyloxycarbonyl)-L-lysinyl]thiazolidine-4-carbonitrile (2.14 g, 3.81 mmol, 82%).

E. (4R)-3-[N$^\alpha$-(tert-Butyloxycarbonyl)-L-lysinyl]thiazolidine-4-carbonitrile (4R)-3-[N$^\alpha$-(tert-Butyloxycarbonyl)-N$^\omega$-(9-fluorenylmethyloxycarbonyl)-L-lysinyl]thiazolidine-4-carbonitrile (1.9 g, 3.4 mmol) was dissolved in THF (40 mL). Diethylamine (10 mL) was added. After 2 h at room temperature the solvent was removed in vacuo. The residue was purified by flash chromatography (eluant: 90% chloroform, 7% methanol, 3% triethylamine) to give a colourless oil identified as (4R)-3-[N$^\alpha$-(tert-butyloxycarbonyl)-L-lysinytothiazolidine-4-carbonitrile (863 mg, 2.5 mmol, 75%).

F. (4R)-3-[N$^\alpha$-(tert-Butyloxycarbonyl)-N$^\omega$-(pyrazinyl-2-carbonyl)-L-lysinyl]thiazolidine-4-carbonitrile (4R)-3-[N$^\alpha$-(tert-Butyloxycarbonyl)-L-lysinyl]thiazolidine-4-carbonitrile (100 mg, 0.29 mmol) was dissolved in CH$_2$Cl$_2$ (20 mL). To this solution at 0° C. 2-pyrazinecarboxylic acid (43 mg, 0.35 mmol) and PyBOP® (170 mg, 0.33 mmol) were added and the pH was adjusted to pH9 with triethylamine. After 18 h at 0° C. to room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 2% methanol, 98% chloroform) to give a colourless oil identified as (4R)-3-[N$^\alpha$-(tert-butyloxycarbonyl)-N$^\omega$-(pyrazinyl-2-carbonyl)-L-lysinyl]thiazolidine-4-carbonitrile (112 mg, 0.25 mmol, 86%).

G. (4R)-3-[N$^\omega$-(Pyrazinyl-2-carbonyl)-L-lysinyl]thiazolidine-4-carbonitrile trifluoroacetate (4R)-3-[N$^\alpha$-(tert-Butyloxycarbonyl)-N$^\omega$-(pyrazinyl-2-carbonyl)-L-lysinyl]thiazolidine-4-carbonitrile (110 mg, 0.26 mmol) was dissolved in trifluoroacetic acid (5 mL). After 1 h at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as (4R)-3-[N$^\omega$-(pyrazinyl-2-carbonyl)-L-lysinyl]thiazolidine-4-carbonitrile trifluoroacetate (57 mg).
[M+H]$^+$=349.1

Example 4

1-[N$^\omega$-(Pyrazinyl-2-carbonyl)-L-ornithinyl]pyrrolidine trifluoroacetate

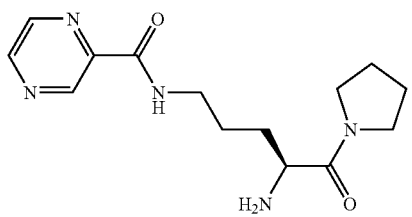

A. 1-[N$^\omega$-(Benzyloxycarbonyl)-N$^\alpha$-(tert-butyloxycarbonyl)-L-ornithinyl]pyrrolidine N$^\omega$-(Benzyloxycarbonyl)-N$^\alpha$-(tert-butyloxycarbonyl)-L-ornithine (5.49 g, 15 mmol) was dissolved in CH$_2$Cl$_2$/DMF (9:1, 100 mL). To this solution at 0° C. was added 1-hydroxybenzotriazole hydrate (3.37 g, 22 mmol), water-soluble carbodiimide (3.46 g, 18 mmol), pyrrolidine (1.28 g, 18 mmol) and triethylamine (200 mg, 20 mmol). After 18 h at 0° C. to room temperature the solvent was removed in vacuo and the residue was taken up in ethyl acetate (200 mL). The solution was washed with 0.3M KHSO$_4$ (2×50 mL), sat. NaHCO$_3$ (2×50 mL), water (2×50 mL) and brine (1×50 mL), dried (Na$_2$SO$_4$) and evaporated in vacuo. The residue was purified by flash chromatography (eluant: 90% ethyl acetate, 10% pet. ether) to give a colourless oil identified as 1-[N$^\omega$-(benzyloxycarbonyl)-N$^\alpha$-(tert-butyloxycarbonyl)-L-ornithinyl]pyrrolidine (5.15 g, 12.3 mmol, 82%).

B. 1-[N$^\alpha$-(tert-Butyloxycarbonyl)-L-ornithinyl]pyrrolidine

1-[N$^\omega$-(Benzyloxycarbonyl)-N$^\alpha$-(tert-butyloxycarbonyl)-L-ornithinyl]pyrrolidine (2.15 g, 5.13 mmol) was dissolved in methanol (80 mL). This solution was hydrogenated over 10% Pd/C (400 mg). After 2 h the catalyst was filtered off and washed with methanol (50 mL). The combined filtrates were evaporated in vacuo to give an off white solid identified as 1-[N$^\alpha$-(tert-butyloxycarbonyl)-L-ornithinyl]pyrrolidine (1.35 g, 4.74 mmol, 94%).

C. 1-[N$^\alpha$-(tert-Butyloxycarbonyl)-N$^\omega$-(pyrazinyl-2-carbonyl)-L-ornithinyl]pyrrolidine 1-[N$^\alpha$-(tert-Butyloxycarbonyl)-L-ornithinyl]pyrrolidine (100 mg, 0.35 mmol) was dissolved in CH$_2$Cl$_2$ (20 mL). To this solution at 0° C. were added PyBroP® (195 mg, 0.4 mmol), 2-pyrazinecarboxylic acid (50 mg, 0.4 mmol) and triethylamine (100 mg, 1.0 mmol). After 18 h at 0° C. to room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 3% methanol, 97% chloroform) to give a sticky white solid identified as 1-[N$^\alpha$-(tert-butyloxycarbonyl)-N$^\omega$-(pyrazinyl-2-carbonyl)-L-ornithinyl]pyrrolidine (90 mg, 0.25 mmol, 66%).

D. 1-[N$^\omega$-(Pyrazinyl-2-carbonyl)-L-ornithinyl]pyrrolidine trifluoroacetate 1-[N$^\alpha$-(tert-Butyloxycarbonyl)-N$^\omega$-(pyrazinyl-2-carbonyl)-L-ornithinyl]pyrrolidine (90 mg, 0.23 mmol) was dissolved in 4M HCl/dioxan (15 mL). After 45 min at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as 1-[N$^\omega$-(pyrazinyl-2-carbonyl)-L-ornithinyl]pyrrolidine trifluoroacetate (51 mg).
[M+H]$^+$=292.1

Example 5

3-[N$^\omega$-(Pyrazinyl-2-carbonyl)-L-ornithinyl]thiazolidine trifluoroacetate

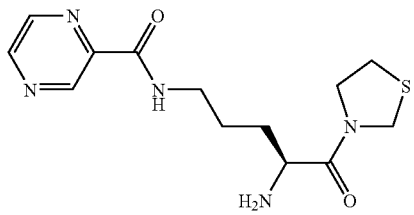

A. 3-[N$^\alpha$-(tert-Butyloxycarbonyl)-N$^\omega$-(9-fluorenylmethyloxycarbonyl)-L-ornithinyl]thiazolidine N$^\alpha$-(tert-Butyloxycarbonyl)-N$^\omega$-(9-fluorenylmethyloxycarbonyl)-L-ornithine (2.73 g, 6 mmol) was dissolved in CH$_2$Cl$_2$/DMF (9:1, 100 mL). To this solution at 0° C. were added 1-hydroxybenzotriazole hydrate (1.53 g, 10 mmol), water-soluble carbodiimide (1.34 g, 7 mmol), thiazolidine (1.28 g, 18 mmol) and triethylamine (80 mg, 8 mmol). After 18 h at 0° C. to room temperature the solvent was removed in vacuo and the residue was taken up in ethyl acetate (100 mL). The solution was washed with 0.3M KHSO$_4$ (2×25 mL), sat. NaHCO$_3$ (2×25 mL), water (2×25 mL) and brine (1×25 mL), dried (Na$_2$SO$_4$) and evaporated in vacuo. The residue was purified by flash chromatography (eluant: 75% ethyl acetate, 25% pet. ether) to give a white solid identified as 3-[N$^\alpha$-(tert-butyloxycarbonyl)-N$^\omega$-(9-fluorenylmethyloxycarbonyl)-L-ornithinyl]thiazolidine (2.55 g, 4.85 mmol, 81%).

B. 3-[N$^\alpha$-(tert-Butyloxycarbonyl)-L-ornithinyl]thiazolidine

3-[N$^\alpha$-(tert-Butyloxycarbonyl)-N$^\omega$-(9-fluorenylmethyloxycarbonyl)-L-ornithinyl]thiazolidine (1.15 g, 2.13 mmol) was dissolved in acetonitrile (20 mL). Diethylamine (5 mL) was added. After 90 min at room temperature the solvent was removed in vacuo and the residue was purified by flash chromatography (eluant: 90% chloroform, 7% methanol, 3% triethylamine) to give a pale yellow oil identified as 3-[N$^\alpha$-(tert-butyloxycarbonyl)-L-ornithinyl]thiazolidine (530 mg, 1.67 mmol, 78%).

C. 3-[N$^\alpha$-(tert-Butyloxycarbonyl)-N$^\omega$-(pyrazinyl-2-carbonyl)-L-ornithinyl]thiazolidine 3-[N$^\alpha$-(tert-Butyloxycarbonyl)-L-ornithinyl]thiazolidine (80 mg, 0.27 mmol) was dissolved in CH$_2$Cl$_2$ (20 mL). To this solution at 0° C. were added PyBroP® (146 mg, 0.3 mmol), 2-pyrazinecarboxylic acid (37 mg, 0.3 mmol) and triethylamine (90 mg, 0.9 mmol). After 18 h at 0° C. to room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 3% methanol, 97% chloroform) to give a sticky white solid identified as 3-[N$^\alpha$-(tert-butyloxycarbonyl)-N$^\omega$-(pyrazinyl-2-carbonyl)-L-ornithinyl]thiazolidine (45 mg, 0.11 mmol, 41%).

D. 3-[N$^\omega$-(Pyrazinyl-2-carbonyl)-L-ornithinyl]thiazolidine trifluoroacetate 3-[N$^\alpha$-(tert-Butyloxycarbonyl)-N$^\omega$-(pyrazinyl-2-carbonyl)-L-ornithinyl]thiazolidine (45 mg, 0.11 mmol) was dissolved in 4M HCl/dioxan (10 mL). After 45 min at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a colourless oil identified as 3-[N$^\omega$-(pyrazinyl-2-carbonyl)-L-ornithinyl]thiazolidine trifluoroacetate (14 mg). [M+H]$^+$=310.0

Example 6

(2S)-1-[N$^\omega$-(2-Chloropyridyl-3-carbonyl)-L-ornithinyl]pyrrolidine-2-carbonitrile trifluoroacetate

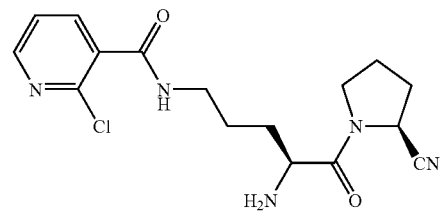

A. (2S)-1-(N$^\alpha$-(tert-Butyloxycarbonyl)-L-ornithinyl)pyrrolidine-2-carbonitrile (2S)-1-(N$^\alpha$-(tert-Butyloxycarbonyl)-L-ornithinyl)pyrrolidine-2-carbonitrile was prepared by the method described for the lysine derivative in Example 2.

B. (2S)-1-(N$^\alpha$-(tert-Butyloxycarbonyl)-N$^\omega$-(2-chloropyridyl-3-carbonyl)-L-ornithinyl)-pyrrolidine-2-carbonitrile (2S)-1-(N$^\alpha$-(tert-Butyloxycarbonyl)-L-ornithinyl)pyrrolidine-2-carbonitrile (80 mg, 0.26 mmol) was dissolved in CH$_2$Cl$_2$ (20 mL). To this solution was added 2-chloropyridine-3-carbonyl chloride (55 mg, 0.32 mmol) and the pH adjusted to pH9 with triethylamine. After 18 h at room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 95% ethyl acetate, 5% pet. ether) to give a colourless oil identified as (2S)-1-(N$^\alpha$-(tert-butyloxycarbonyl)-N$^\omega$-(2-chloropyridyl-3-carbonyl)-L-ornithinyl)pyrrolidine-2-carbonitrile (60 mg, 0.14 mmol, 53%).-

C. (2S)-1-[N^ω-(2-Chloropyridyl-3-carbonyl)-L-ornithinyl]pyrrolidine-2-carbonitrile trifluoroacetate (2S)-1-(N^α-(tert-Butyloxycarbonyl)-N^ω-(2-chloropyridyl-3-carbonyl)-L-ornithinyl]pyrrolidine-2-carbonitrile (60 mg, 0.14 mmol) was dissolved in trifluoroacetic acid (5 mL). After 1 h at room temperature the solvent was removed in vacuo. The residue was purified by preparative hplc (Vydac C18, 5 to 50% 0.1% TFA/acetonitrile into 0.1% TFA/water over 40 min at 3 mL/min). Fractions containing the product were lyophilised to give a white solid identified as (2S)-1-[N^ω-(2-chloropyridyl-3-carbonyl)-L-ornithinyl]pyrrolidine-2-carbonitrile trifluoroacetate (52 mg).

$[M+H]^+ = 350.1$

Example 7

1-[N^ω-(2-Chloropyridyl-3-carbonyl)-L-ornithinyl]pyrrolidine hydrochloride

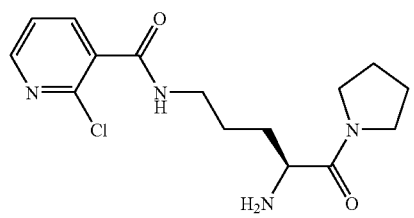

A. 1-(N^α-(tert-Butyloxycarbonyl)-N^ω-(2-chloropyridyl-3-carbonyl)-L-ornithyl)-pyrrolidine 1-(N^α-(tert-Butyloxycarbonyl)-L-ornithyl)pyrrolidine (20 mg, 0.069 mmol) was dissolved in CH$_2$Cl$_2$ (5 mL). To this solution was added 2-chloropyridine-3-carbonyl chloride (14 mg, 0.076 mmol) and the pH adjusted to pH9 with triethylamine. After 1 h at room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 10% methanol, 90% dichloromethane) to give a colourless oil identified as 1-(N^α-(tert-butyloxycarbonyl)-N^ω-(2-chloropyridyl-3-carbonyl)-L-ornithyl)pyrrolidine (19 mg, 0.045 mmol, 63%).

B. 1-[N^ω-(2-Chloropyridyl-3-carbonyl)-L-ornithinyl]pyrrolidine hydrochloride 1-[N^α-(tert-Butyloxycarbonyl)-N^ω-(2-chloropyridyl-3-carbonyl)-L-ornithinyl]pyrrolidine (19 mg, 0.045 mmol) was dissolved in 4M HCl/dioxan (10 mL). After 45 min at room temperature the solvent was removed in vacuo to give a white solid identified as 1-[N^ω-(2-chloropyridyl-3-carbonyl)-L-ornithinyl]pyrrolidine hydrochloride (15 mg).

$[M+H]^+ = 325.1$

Example 8

3-[N^ω-(2-Chloropyridyl-3-carbonyl)-L-ornithinyl]thiazolidine hydrochloride

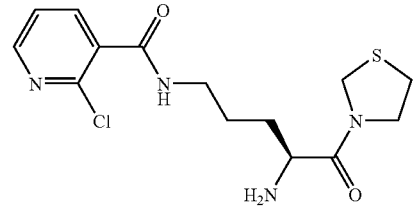

A. 3-(N^α-(tert-Butyloxycarbonyl)-N^ω-(2-chloropyridyl-3-carbonyl)-L-ornithyl)-thiazolidine 3-(N^α-(tert-Butyloxycarbonyl)-L-ornithyl)thiazolidine (136 mg, 0.45 mmol) was dissolved in CH$_2$Cl$_2$ (10 mL). To this solution was added 2-chloropyridine-3-carbonyl chloride (88 mg, 0.5 mmol) and the pH adjusted to pH9 with triethylamine. After 1 h at room temperature the solvent was removed in vacuo and the residue was taken up in ethyl acetate (70 mL). The solution was washed with 0.3M KHSO$_4$ (2×20 mL), sat. NaHCO$_3$ (2×20 mL), water (2×20 mL) and brine (1×20 mL), dried (Na$_2$SO$_4$) and evaporated in vacuo. The residue was purified by flash chromatography (eluant: 1.5% methanol, 98.5% dichloromethane) to give a colourless oil identified as 3-(N^α-(tert-butyloxycarbonyl)-N^ω-(2-chloropyridyl-3-carbonyl)-L-ornithyl)thiazolidine (30 mg, 0.068 mmol, 15%).

B. 3-[N^ω-(2-Chloropyridyl-3-carbonyl)-L-ornithinyl]thiazolidine hydrochloride 3-[N^α-(tert-Butyloxycarbonyl)-N^ω-(2-chloropyridyl-3-carbonyl)-L-ornithinyl]thiazolidine (30 mg, 0.068 mmol) was dissolved in 4M HCl/dioxan (10 mL). After 45 min at room temperature the solvent was removed in vacuo to give a white solid identified as 1-[N^ω-(2-chloropyridyl-3-carbonyl)-L-ornithinyl]thiazolidine hydrochloride (25 mg).

$[M+H]^+ = 342.1$

Example 9

3-[N^ω-(5-Cyano-2-pyridyl)-L-lysinyl]thiazolidine hydrochloride

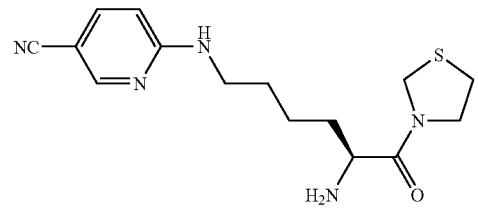

A. 3-(N$^\alpha$-(tert-Butyloxycarbonyl)lysinyl)thiazolidine 3-(N$^\alpha$-(tert-Butyloxycarbonyl)lysinyl)thiazolidine was prepared in two steps following the method described for the corresponding ornithine derivative in Example 5.

B. 3-[N$^\alpha$-(tert-Butyloxycarbonyl)-N$^\omega$-cyano-2-pyridyl)-L-lysinyl]thiazolidine 3(N$^\alpha$-(tert-Butyloxycarbonyl)lysinyl)thiazolidine (52 mg, 0.165 mmol) was dissolved in DMF (10 mL). 6-Chloronicotinonitrile (22.8 mg, 0.165 mmol) and potassium carbonate (45.8 mg, 0.3 mmol) were added. The reaction mixture was stirred at 70° C. for 18 hours and the solvent removed in vacua. The residue was purified by flash chromatography (eluant: 97% chloroform, 3% methanol) to give a colourless oil identified as 3-[N$^\alpha$-(tert-butyloxycarbonyl)-N$^\omega$-(5-cyan2-pyridyl))-L-lysinyl]thiazolidine (30 mg, 0.067 mmol, 43%).

C. 3-[N$^\omega$-(5-Cyano-2-pyridyl)-L-lysinyl]thiazolidine hydrochloride

3-[N$^\omega$-(tert-Butyloxycarbonyl)-N$^\omega$-(5-cyano-2-pyridyl))-L-lysinyl]thiazolidine (30 mg, 0.067 mmol) was dissolved in 4M HCl/dioxan (20 mL). After 1 hour at room temperature the solvent was removed in vacuo to give a white solid identified as 3-[N$^\omega$-(5-cyano-2-pyridyl))-L-lysinyl]thiazolidine hydrochloride (24 mg, 0.067 mmol, 100%).
[M+H]$^+$=348.2

Example 10

(2S)-1-[N$^\omega$-(5-Cyano-2-pyridyl)-L-lysinyl]pyrrolidine-2-carbonitrile trifluoroacetate

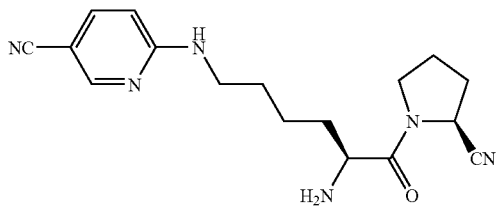

A. (2S)-1-[N$^\alpha$-(tert-Butyloxycarbonyl)-N$^\omega$-(5-cyano-2-pyridyl)-L-lysinyl]pyrrolidine-2-carbonitrile (2S)-1-(N$^\alpha$-(tert-Butyloxycarbonyl)lysinyl)pyrrolidine-2-carbonitrile (150 mg, 0.46 mmol) was dissolved in DMF (10 mL). 6-Chloronicotinonitrile (70 mg, 0.51 mmol) and potassium carbonate (130 mg,0.94 mmol) were added. The reaction mixture was stirred at 70° C. for 18 hours and the solvent removed in vacuo. The residue was purified by flash chromatography (eluant: 97% chloroform, 3% :methanol) to give a colourless oil identified as (2S)-1-[N$^\alpha$-(tert-butyloxycarbonyl)-N$^\omega$-(5-cyano-2-pyridyl))-L-lysinyl]pyrrolidine-2-carbonitrile (71 mg, 0.17 mmol, 37%).

B. (2S)-1-[N$^\omega$-(5-Cyano-2-pyridyl)-L-lysinyl]pyrrolidine-2-carbonitrile trifluoroacetate (2S)-1-[N$^\alpha$-(tert-Butyloxycarbonyl)-N$^\omega$-(5-cyano-2-pyridyl))-L-lysinyl]pyrrolidine-2-carbonitrile (71 mg, 0.17 mmol) was dissolved in 4M HCl/dioxan (20 mL). After 1 hour at room temperature the solvent was removed in vacuo to give a white solid identified as (2S)-1-[N$^\omega$-(5-cyano-2-pyridyl))-L-lysinyl]pyrrolidine-2-carbonitrile hydrochloride (62 mg 0.17 mmol, 100%).
[M+H]$^+$=327.1

Example 11

(2S)-1-[N$^\omega$-(5-Trifluoromethyl-2-pyridyl)-L-ornithinyl]pyrrolidine-2-carbonitrile trifluoroacetate

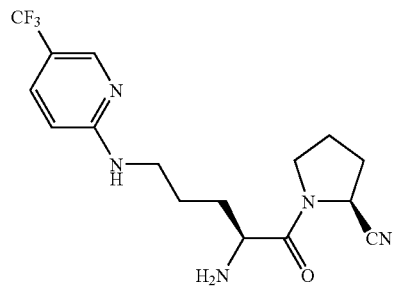

A. (2S)-1-[N$^{60}$-(tert-Butyloxycarbonyl)-N$^\omega$-(5-trifluoromethyl-2-pyridyl)-L-ornithinyl]-pyrrolidine-2-carbonitrile (2S)-1-[N$^\alpha$-(tert-Butyloxycarbonyl)ornithinyl]pyrrolidine-2-carbonitrile (140 mg, 0.45 mmol) was dissolved in DMF (10 mL). 2-Chloro-5-(trifluoromethyl)pyridine (90 mg, 0.49 mmol) and potassium carbonate (130 mg, 0.92 mmol) were added. The reaction mixture was stirred at 70° C. for 18 hours and the solvent removed in vacuo. The residue was purified by flash chromatography (eluant: 97% chloroform, 3% methanol) to give a colourless oil identified as (2S)-1-[N$^\alpha$-(tert-butyloxycarbonyl)-N$^\omega$-(5-trifluoromethyl-2-pyridyl))-L-ornithinyl]-pyrrolidine-2-carbonitrile (58 mg, 0.13 mmol, 28%).

B. (2S)-1-[N$^\omega$-(5-Trifluoromethyl-2-pyridyl))-L-ornithinyl]pyrrolidine-2-carbonitrile trifluoroacetate (2S)-1-[N$^\alpha$-(tert-Butyloxycarbonyl)-[N$^\omega$-(5-trifluoromethyl-2-pyridyl)-L-ornithinyl]pyrrolidine-2-carbonitrile (58 mg, 13 mmol) was dissolved in 4M HCl/dioxan (20 mL). After 1 hour at room temperature the solvent was removed in vacuo to give a white solid identified as (2S)-1-[N$^\omega$-(5-trifluoromethyl-2-pyridyl))-L-ornithinyl]pyrrolidine-2-carbonitrile hydrochloride (51 mg, 0.13 mmol, 100%).
[M+H]$^+$=356.2

Example 12

3-[N$^\omega$-(2-Quinolinylmethyl)-L-lysinyl]thiazolidine hydrochloride

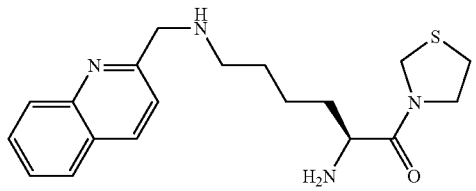

A. 3-[N$^\alpha$-(tert-Butyloxycarbonyl)-N$^\omega$-(2-quinolinylmethyl)-L-lysinyl]thiazolidine 3-[N$^\alpha$-(tert-Butyloxycarbonyl)lysinyl]thiazolidine (100 mg, 0.32 mmol) was dissolved in methanol (10 mL). 2-Quinolinecarboxaldehyde (61 mg, 0.39 mmol) was added. After 1 hour sodium acetoxyborohydride (138 mg, 0.65 mmol) was added. The reaction mixture was stirred at room temperature for 18 hours and the solvent removed in vacuo. The residue was purified by flash chromatography (eluant: 93% chloroform, 7% methanol) to give a colourless oil identified as 3-[N$^\alpha$-(tert-butyloxycarbonyl)-N$^\omega$-(2-quinolinylmethyl)-L-lysinyl]thiazolidine (38 mg, 0.083 mmol, 26%).

B. 3-[N$^\omega$-(2-Quinolinylmethyl)-L-lysinyl]thiazolidine hydrochloride

3-[N$^\alpha$-(tert-Butyloxycarbonyl)-N$^\omega$-(2-quinolinylmethyl)-L-lysinyl]thiazolidine (38 mg, 0.083 mmol) was dissolved in 4M HCl/dioxan (20 mL). After 1 hour at room temperature the solvent was removed in vacuo to give a white solid identified as 3-[N$^\omega$-(2-quinolinylmethyl)-L-lysinyl]thiazolidine hydrochloride (31 mg, 0.078 mmol, 94%).

[M+H]$^+$=358.2

Example 13

3-[N$^\omega$-(2-Quinolinylmethyl)-L-ornithinyl]thiazolidine hydrochloride

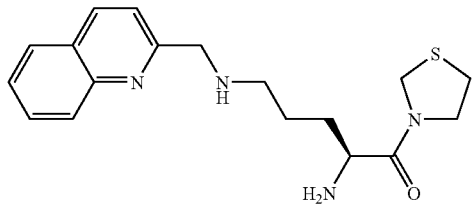

A. 3-[N$^\alpha$-(tert-Butyloxycarbonyl)-N$^\omega$-(2-quinolinylmethyl)-L-ornithinyl]thiazolidine 3-[N$^\alpha$-(tert-Butyloxycarbonyl)ornithinyl]thiazolidine (98 mg, 0.33 mmol) was dissolved in methanol (10 mL). 2-Quinolinecarboxaldehyde (52 mg, 0.33 mmol) was added. After 1 hour sodium acetoxyborohydride (119 mg, 0.56 mmol) was added. The reaction mixture was stirred at room temperature for 18 hours and the solvent removed in vacuo. The residue was purified by flash chromatography (eluant: 93% chloroform, 7% methanol) to give a colourless oil identified as 3-[N$^\alpha$-(tert-butyloxycarbonyl)-N$^\omega$-(2-quinolinylmethyl)-L-ornithinyl]thiazolidine (45 mg, 0.10 mmol, 36%).

B. 3-[N$^\omega$-(2-Quinolinylmethyl)-L-ornithinyl]thiazolidine hydrochloride 3-[N$^\alpha$-(tert-Butyloxycarbonyl)-N$^\omega$-(2-quinolinylmethyl)-L-ornithinyl]thiazolidine (45 mg, 0.1 mmol) was dissolved in 4M HCl/dioxan (20 mL). After 1 hour at room temperature the solvent was removed in vacuo to give a white solid identified as 3-[N$^\omega$-(2-quinolinylmethyl)-L-ornithinyl]thiazolidine hydrochloride (38 mg, 0.098 mmol, 98%).

[M+H]$^+$=345.2

Example 14

3-[N$^\omega$-(2-Quinoxaloyl)-L-lysinyl]thiazolidine hydrochloride

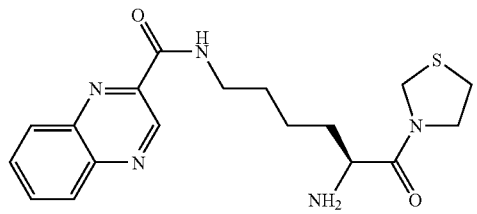

A. 3-[N$^\alpha$-(tert-Butyloxycarbonyl)-N$^\omega$-(2-quinoxaloyl)-L-lysinyl]thiazolidine 3-[N$^\alpha$-(tert-Butyloxycarbonyl)lysinyl]thiazolidine (128 mg, 0.4 mmol) was dissolved in CH$_2$Cl$_2$ (10 mL). 2-Quinoxaloyl chloride (85 mg, 0.44 mmol) and potassium carbonate (45.8 mg, 0.3 mmol) were added. The reaction mixture was stirred at room temperature for 18 hours and the solvent removed in vacuo. The residue was purified by flash chromatography (eluant: 99.5% chloroform, 0.5% methanol) to give a colourless oil identified as 3-[N$^\alpha$-(tert-butyloxycarbonyl)-N$^\omega$-(2-quinoxaloyl)-L-lysinyl]thiazolidine (140 mg, 0.296 mmol, 74%).

B. 3-[N$^\omega$-(2-Quinoxaloyl)-L-lysinyl]thiazolidine hydrochloride

3-[N$^\alpha$-(tert-Butyloxycarbonyl)-N$^\omega$-(2-quinoxaloyl)-L-lysinyl]thiazolidine (140 mg, 0.296 mmol was dissolved in 4M HCl/dioxan (20 mL). After 1 hour at room temperature the solvent was removed in vacuo to give a white solid identified as 3-[N$^\omega$-(2quinoxaloyl)-L-lysinyl]thiazolidine hydrochloride (128 mg, 0.296 mmol, 100%).

[M+H]$^+$=374.2

The Examples set out in the following Tables were prepared by analogous methods to the above.

TABLE 1

Examples 15–36

[Structure: Het-C(=O)-NH-CH2CH2CH2-CH(NH2)-C(=O)-N(pyrrolidine with X¹ and CN)]

| Example | Het | X¹ |
|---------|-----|-----|
| 15 | pyridin-3-yl | CH₂ |
| 16 | pyridin-3-yl | S |
| 17 | pyridin-2-yl | CH₂ |
| 18 | pyridin-4-yl | CH₂ |
| 19 | 2-chloro-4-trifluoromethyl-pyrimidin-5-yl | CH₂ |
| 20 | 5-methyl-pyrazin-2-yl | CH₂ |
| 21 | 5-bromo-pyridin-3-yl | CH₂ |
| 22 | 2-chloro-4-methyl-pyridin-3-yl | CH₂ |

TABLE 1-continued

Examples 15–36

| Example | Het | X¹ |
|---------|-----|-----|
| 23 | 2-chloro-6-methyl-pyridin-4-yl | CH₂ |
| 24 | 6-trifluoromethyl-pyridin-3-yl | CH₂ |
| 25 | 4-chloro-pyridin-3-yl | CH₂ |
| 26 | 2,4-dimethyl-thiazol-5-yl | CH₂ |
| 27 | isoxazol-5-yl | CH₂ |
| 28 | 6-chloro-pyridin-2-yl | CH₂ |
| 29 | 3-chloro-5-trifluoromethyl-pyridin-2-yl | CH₂ |
| 30 | 6-cyano-pyridin-3-yl | CH₂ |

TABLE 1-continued
Examples 15–36
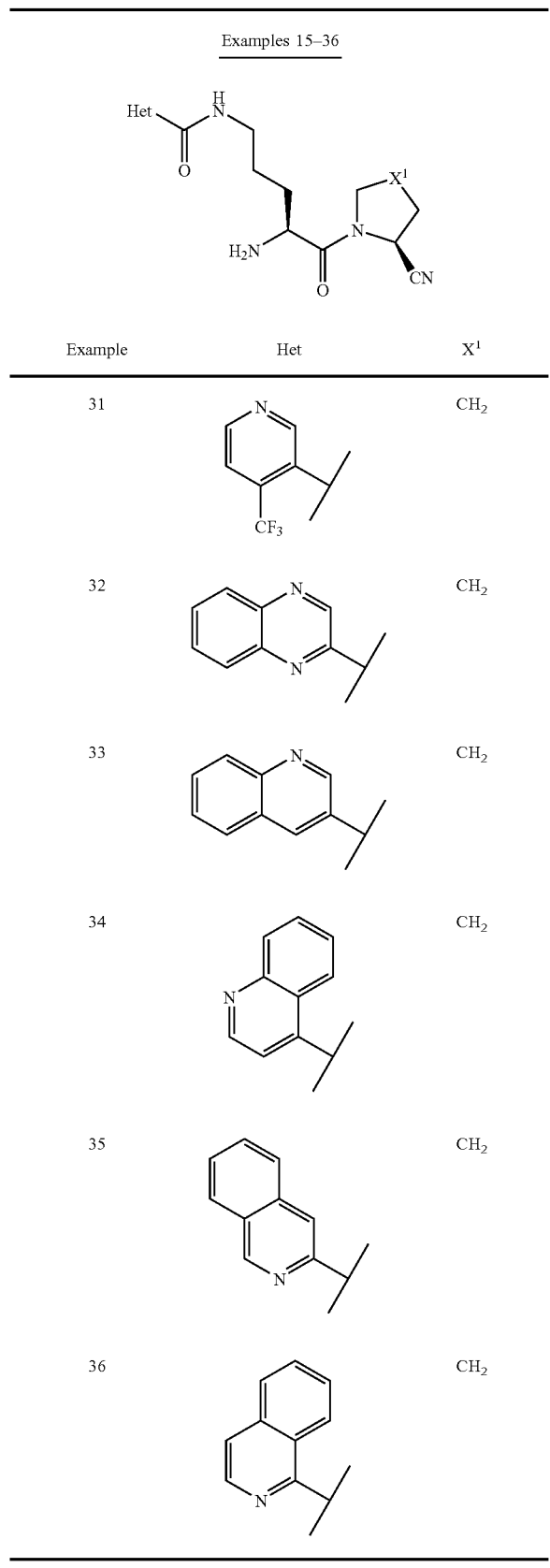
TABLE 2
Examples 37–58
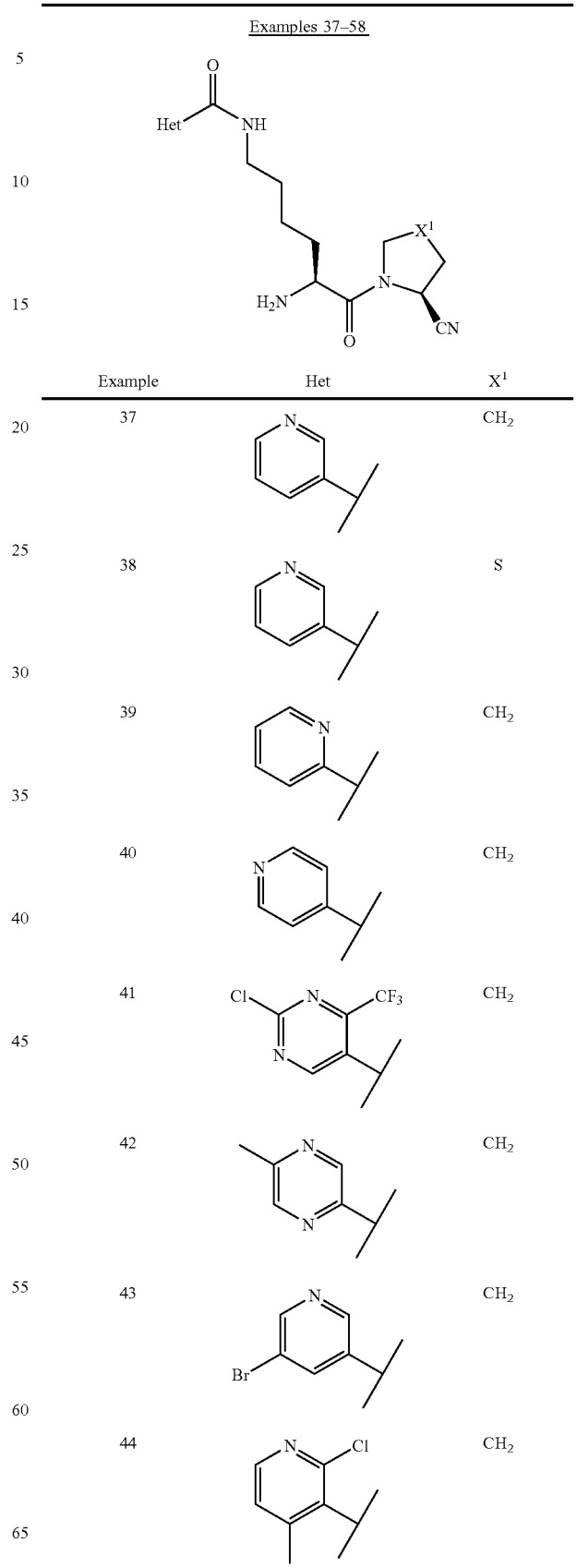

TABLE 2-continued

Examples 37–58

| Example | Het | X¹ |
|---|---|---|
| 45 | 2-chloro-6-methylpyridin-4-yl | CH₂ |
| 46 | 6-trifluoromethylpyridin-3-yl | CH₂ |
| 47 | 4-chloropyridin-3-yl | CH₂ |
| 48 | 2,4-dimethylthiazol-5-yl | CH₂ |
| 49 | isoxazol-5-yl | CH₂ |
| 50 | 6-chloropyridin-2-yl | CH₂ |
| 51 | 3-chloro-5-trifluoromethylpyridin-2-yl | CH₂ |
| 52 | 6-cyanopyridin-3-yl | CH₂ |
| 53 | 4-trifluoromethylpyridin-3-yl | CH₂ |
| 54 | quinoxalin-2-yl | CH₂ |
| 55 | quinolin-3-yl | CH₂ |
| 56 | quinolin-4-yl | CH₂ |
| 57 | isoquinolin-3-yl | CH₂ |

TABLE 2-continued
Examples 37–58
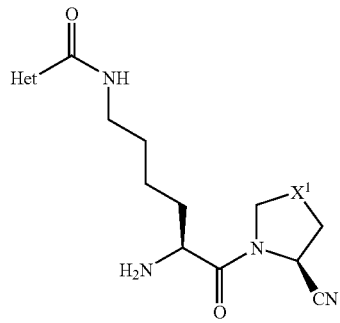
| Example | Het | X¹ |
|---|---|---|
| 58 | 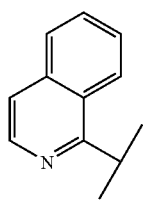 | CH₂ |
TABLE 3
Examples 59–91
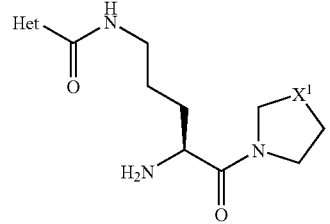
| Example | Het | X¹ |
|---|---|---|
| 59 | 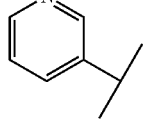 | S |
| 60 | | CH₂ |
| 61 | | S |
| 62 | | S |
TABLE 3-continued
Examples 59–91
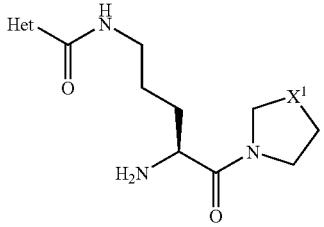
| Example | Het | X¹ |
|---|---|---|
| 63 | | S |
| 64 | | S |
| 65 | | S |
| 66 | | S |
| 67 | | S |
| 68 | | S |
| 69 | | S |
| 70 | 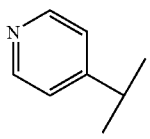 | S |

TABLE 3-continued

Examples 59–91

[Structure: Het-C(=O)-NH-CH2CH2CH2-CH(NH2)-C(=O)-N(pyrrolidine with X¹)]

| Example | Het | X¹ |
|---------|-----|-----|
| 71 | 2,6-dichloropyridin-3-yl | S |
| 72 | 6-(trifluoromethyl)-2-methylpyridin-3-yl | S |
| 73 | 2,6-dimethoxypyridin-3-yl | S |
| 74 | 2,6-dichloropyridin-3-yl | CH₂ |
| 75 | 3-chloro-2-methoxypyridin-5-yl | S |
| 76 | 2,4-dimethylthiazol-5-yl | S |
| 77 | isoxazol-5-yl | S |
| 78 | 6-chloropyridin-2-yl | S |

TABLE 3-continued

Examples 59–91

[Structure: Het-C(=O)-NH-CH2CH2CH2-CH(NH2)-C(=O)-N(pyrrolidine with X¹)]

| Example | Het | X¹ |
|---------|-----|-----|
| 79 | 3-chloro-5-(trifluoromethyl)pyridin-2-yl | S |
| 80 | 6-cyanopyridin-3-yl | S |
| 81 | 4-(trifluoromethyl)pyridin-3-yl | S |
| 82 | 6-(trifluoromethyl)pyridin-3-yl | S |
| 83 | 4-chloropyridin-3-yl | S |
| 84 | quinoxalin-2-yl | S |
| 85 | quinolin-3-yl | S |

TABLE 3-continued
Examples 59–91
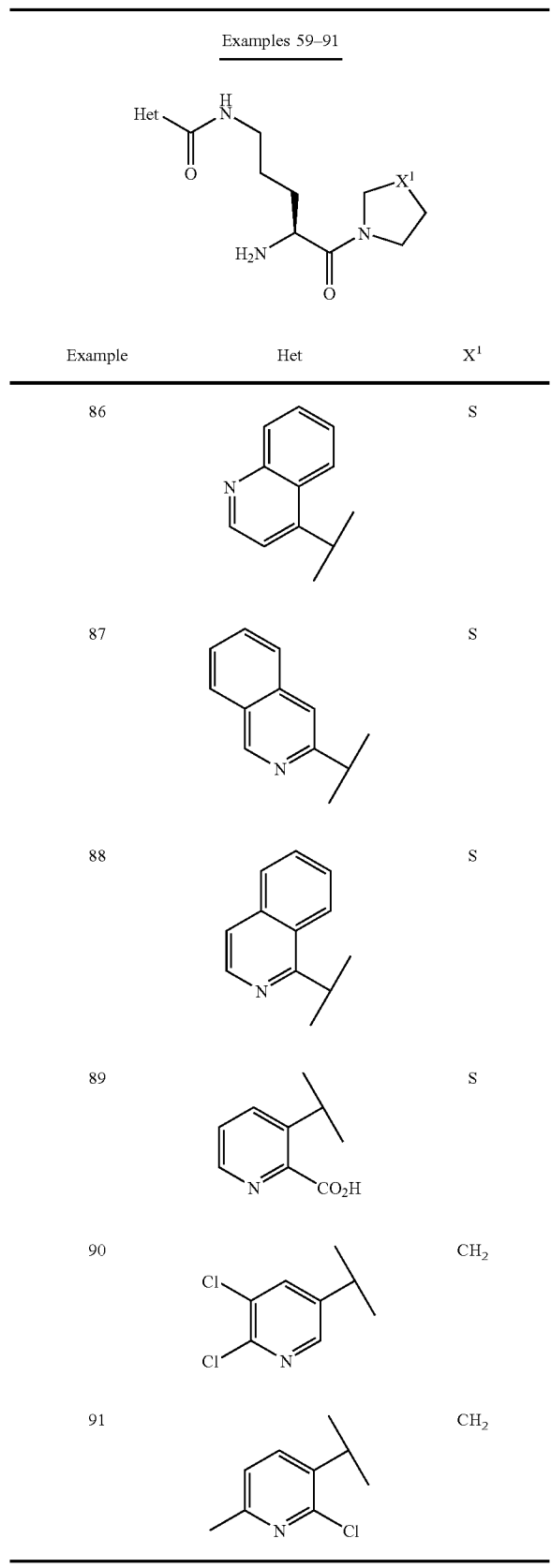
TABLE 4
Examples 92–115
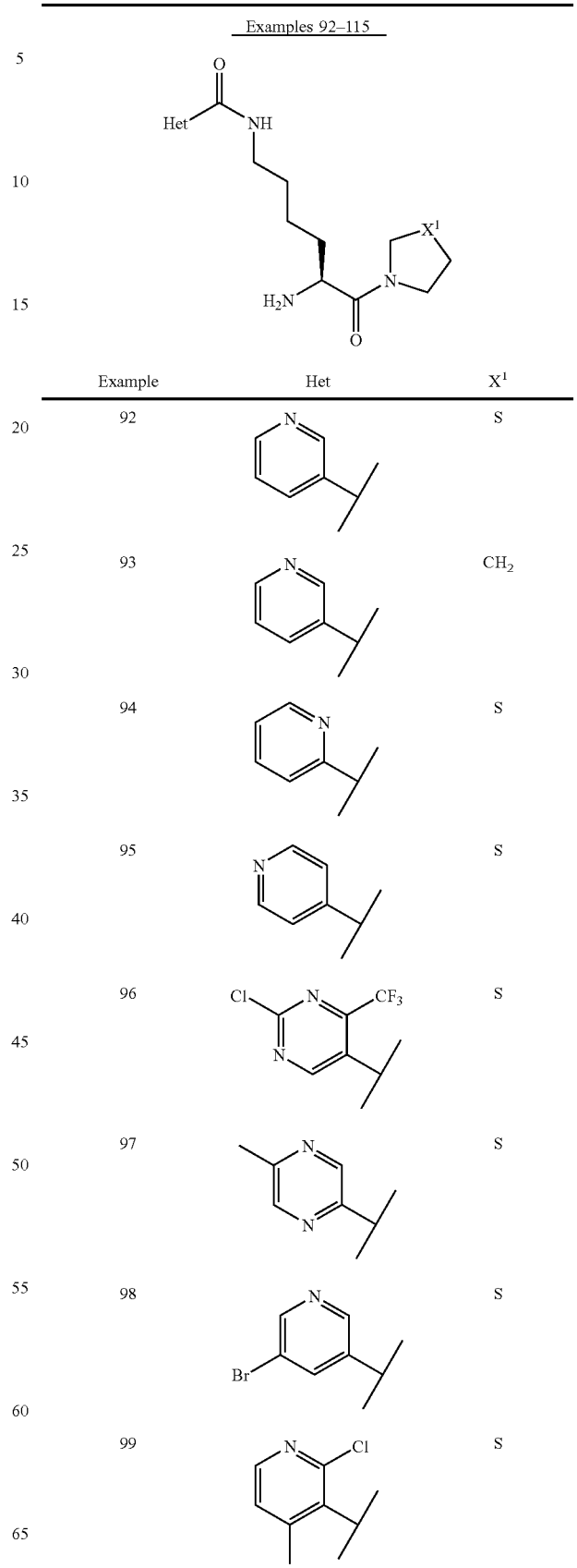

TABLE 4-continued

Examples 92–115

| Example | Het | X¹ |
|---------|-----|-----|
| 100 | 2-chloro-6-methyl-4-pyridyl | S |
| 101 | 3-pyridyl-2-carboxylic acid | S |
| 102 | 3-chloro-2-hydroxy-5-pyridyl | S |
| 103 | 2,3-dichloro-5-pyridyl | S |
| 104 | 2,4-dimethyl-thiazol-5-yl | S |
| 105 | isoxazol-5-yl | S |
| 106 | 6-chloro-2-pyridyl | S |
| 107 | 3-chloro-5-trifluoromethyl-2-pyridyl | S |
| 108 | 6-cyano-3-pyridyl | S |
| 109 | 4-trifluoromethyl-3-pyridyl | S |
| 110 | 6-trifluoromethyl-3-pyridyl | S |
| 111 | 4-chloro-3-pyridyl | S |
| 112 | quinolin-3-yl | S |
| 113 | isoquinolin-1-yl | S |

TABLE 4-continued

Examples 92–115

| Example | Het | X¹ |
|---|---|---|
| 114 | (quinolin-4-yl) | S |
| 115 | (isoquinolin-3-yl) | S |

TABLE 5

Examples 116–120

| Example | Het | X¹ |
|---|---|---|
| 116 | (4-cyanopyridin-3-yl) | S |
| 117 | (6-(ethoxycarbonyl)pyridin-3-yl, EtO₂C-) | S |
| 118 | (5-cyanopyridin-2-yl, NC-) | S |
| 119 | (3-cyanopyrazin-2-yl) | S |
| 120 | (5-(trifluoromethyl)pyridin-2-yl, CF₃-) | S |

Example 121

Determination of Activity in vitro

Compounds were assayed as inhibitors of DP-IV according to the methods described in WO95/15309. All the compounds described in the foregoing Examples were competitive inhibitors of DP-IV with $K_i$ values less than 300 nM.

Example 122

Determination of Activity in vivo

The anti-diabetic action of selected compounds was demonstrated in Zucker obese rats using a standard oral glucose tolerance test. Control rats were given a solution of glucose by oral gavage, and plasma glucose levels were determined. These rats demonstrated a significant hyperglycaemia. Compounds according to the present invention were dissolved in glucose solution at various concentrations, such that the rats could be given varying doses of the compound simultaneously with the glucose challenge. The hyperglycaemic excursion was reduced in a dose-dependent manner in animals receiving between 0.1 and 100 mg/kg of DP-IV inhibitor.

Example 123

Pharmaceutical Formulation

Tablets containing 100 mg of the compound of Example 1 as the active agent are prepared from the following:

| | |
|---|---:|
| Compound of Example 1 | 200.0 g |
| Corn starch | 71.0 g |
| Hydroxypropylcellulose | 18.0 g |
| Carboxymethylcellulose calcium | 13.0 g |
| Magnesium stearate | 3.0 g |
| Lactose | 195.0 g |
| Total | 500.0 g |

The materials are blended and then pressed to give 2000 tablets of 250 mg, each containing 100 mg of the compound of Example 1.

The above demonstrates that the compounds according to the present invention are inhibitors of DP-IV in vitro and effective anti-hyperglycaemic agents in vivo. They would accordingly be expected to be useful as therapeutic agents for the treatment of impaired glucose tolerance, type II diabetes, and other diseases where inhibition of this enzyme leads to an improvement in the underlying pathology or the symptoms.

The present invention is further defined in the following Claims.

What is claimed is:

1. A compound selected from compounds of formula 1, tautomers and stereoisomers, diastereoisomers, enantiomers and epimers thereof, and pharmaceutically acceptable salts of said compounds, tautomers, stereoisomers, diastereoisomers, enantiomers and epimers,

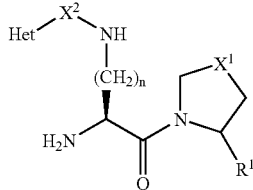

wherein:
$R^1$ is either a hydrogen atom or a nitrile group;
$X^1$ is selected from a sulphur atom, an oxygen atom, a sulphonyl group and a methylene group;
$X^2$ is a carbonyl group, a methylene group or a covalent bond;
Het is an aromatic nitrogen-containing heterocycle selected from pyridyl, pyridazinyl, pyrimidinyl, pyrazinyl, imidazolyl, pyrazolyl, thiazolyl, isothiazolyl, oxazolyl, isoxazolyl and benz-fused analogues thereof, all of which may optionally be substituted on one or more carbon atoms, and where the substituents are selected from $C_1$–$C_6$ alkyl, hydroxy, $C_1$–$C_6$ alkyloxy, amino, $C_1$–$C_6$ alkylamino, di($C_1$–$C_6$ alkyl)amino, fluoro, chloro, bromo, trifluoromethyl, nitro, cyano, carboxy and $C_1$–$C_6$ alkyloxycarbonyl groups; and
n is 1–5.

2. A compound according to claim 1 wherein $R^1$ is a nitrile group.

3. A compound according to claim wherein the stereochemistry of the nitrile group is as shown in formula 2

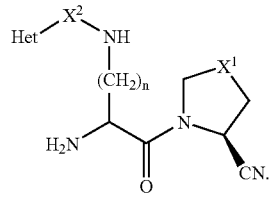

4. A compound according to claim 1 wherein the stereochemistry of the centre adjacent to the primary amine is of the S configuration as shown in formula 3

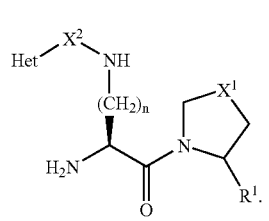

5. A compound according to claim 4 wherein $R^1$ is a nitrile group and the stereochemistry of the nitrile group is as shown in formula 4

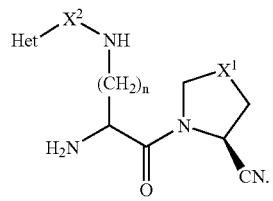

6. A compound according to claim 1 wherein $X^1$ is selected from a sulphur atom and a methylene group.
7. A compound according to claim 1 wherein n is 3 or 4.
8. A compound according to claim 1 selected from:
(4R)-3-[$N^\omega$-(Pyrazinyl-2-carbonyl)-L-lysinyl]thiazolidine-4-carbonitrile,
3-[$N^\omega$-(2-Chloropyridyl-3-carbonyl)-L-ornithinyl]thiazolidine,
3-[$N^\omega$-(Pyrazinyl-2-carbonyl)-L-ornithinyl]thiazolidine,
3-[$N^\omega$-(5-Cyano-2-pyridyl)-L-lysinyl]thiazolidine,
(2S)-1-[$N^\omega$-(5-Cyano-2-pyridyl)-L-lysinyl]pyrrolidine-2-carbonitrile,
(2S)-1-[$N^\omega$-(5-Trifluoromethyl-2-pyridyl)-L-ornithinyl]pyrrolidine-2-carbonitrile,
3-[$N^\omega$-(2-Quinolinylmethyl)-L-lysinyl]thiazolidine,
3-[$N^\omega$-(2-Quinolinylmethyl)-L-ornithinyl]thiazolidine,
3-[$N^\omega$-(2Quinoxaloyl)-L-lysinyl]thiazolidine,
3-[$N^\omega$-(2-Quinoxaloyl)-L-ornithinyl]thiazolidine,
(2S)-1-[$N^\omega$-(2-Quinoxaloyl)-L-ornithinyl]pyrrolidine-2-carbonitrile,
3-[$N^\omega$-(6-Methylpyrazinyl-2-carbonyl)-L-ornithinyl]thiazolidine,
3-[$N^\omega$-(Isoquinoline-3-carbonyl)-L-ornithinyl]thiazolidine, and
3-[$N^\omega$-(6-Trifluoromethylnicotinoyl)-L-ornithinyl]thiazolidine.

9. A pharmaceutical composition for human therapeutic use comprising at least one compound according to claim 1.

10. A method of treatment of at least one condition selected from the group consisting of type 2 diabetes, and impaired glucose tolerance which comprises the administration to a patient in need of such treatment of a therapeutically effective amount of a compound according to claim 1.

* * * * *